United States Patent
Demuth et al.

(10) Patent No.: US 6,303,661 B1
(45) Date of Patent: Oct. 16, 2001

(54) USE OF DIPEPTIDYL PEPTIDASE IV EFFECTORS FOR LOWERING THE BLOOD GLUCOSE LEVEL IN MAMMALS

(75) Inventors: Hans-Ulrich Demuth, Halle; Fred Rosche, Dieskau; Joem Schmidt, Halle, all of (DE); Robert P. Pauly, Vancouver (CA); Christopher H. S. McIntosh, Vancouver (CA); Ray A. Pederson, Vancouver (CA)

(73) Assignee: Probiodrug, Weinbergweg (DE)

( * ) Notice: Subject to any disclaimer, the term of this patent is extended or adjusted under 35 U.S.C. 154(b) by 0 days.

(21) Appl. No.: 09/155,833

(22) PCT Filed: Apr. 24, 1997

(86) PCT No.: PCT/DE97/00820

§ 371 Date: Oct. 7, 1998

§ 102(e) Date: Oct. 7, 1998

(87) PCT Pub. No.: WO97/40832

PCT Pub. Date: Nov. 6, 1997

(30) Foreign Application Priority Data

Apr. 25, 1996 (DE) .............................................. 196 16 486

(51) Int. Cl.[7] .......................... A61K 38/48; A61K 38/05
(52) U.S. Cl. ...................... 514/866; 514/19; 514/183; 424/94.63
(58) Field of Search ...................... 424/94.63; 514/19, 514/183, 866

(56) References Cited

U.S. PATENT DOCUMENTS

| 2,961,377 | 11/1960 | Shapiro et al. ........................ 167/65 |
|---|---|---|
| 3,960,949 | 6/1976 | Ahrens et al. ...................... 260/564 B |
| 4,935,493 | 6/1990 | Bachovchin et al. ................ 530/331 |
| 5,433,955 | 7/1995 | Bredehorst et al. ................ 424/92.3 |
| 5,462,928 | * 10/1995 | Bachovchin et al. ................ 514/19 |
| 5,512,549 | 4/1996 | Chen et al. ........................... 514/12 |
| 5,543,396 | * 8/1996 | Powers et al. ........................ 514/19 |
| 5,614,379 | 3/1997 | MacKellar ........................ 435/68.1 |
| 5,624,894 | 4/1997 | Bodor ..................................... 514/2 |
| 5,939,560 | * 8/1999 | Jenkins et al. ...................... 548/535 |
| 6,006,753 | 12/1999 | Efendic ................................ 128/898 |

FOREIGN PATENT DOCUMENTS

| 25 42598 A1 | 10/1974 | (DE) ........................... C07C/129/16 |
|---|---|---|
| 296075 | 8/1989 | (DE) . |
| 0658568A1 | 12/1994 | (DE) . |
| 0708179A2 | 10/1995 | (DE) . |
| 19616486 | 10/1997 | (DE) ........................... A61K/39/395 |
| 2085665 | 3/1971 | (FR) ............................. A61K/27/00 |
| 2696740 | 10/1992 | (FR) ......................... C07D/207/404 |
| 4334357 | 11/1992 | (JP) ............................ C07C/233/57 |
| 9308259 A2 | 4/1993 | (WO) . |
| 9511689 | 5/1995 | (WO) ........................... A61K/37/00 |
| 9515309 | 6/1995 | (WO) ........................... C07D/207/16 |
| 9529691 | 11/1995 | (WO) ........................... A61K/31/675 |
| 9740832 | 11/1997 | (WO) ........................... A61K/31/425 |
| 9745117 | 12/1997 | (WO) ........................... A61K/31/435 |
| 9822494 | 5/1998 | (WO) ............................... C07K/5/00 |
| WO 00/53171 | 9/2000 | (WO) ........................... A61K/31/155 |

OTHER PUBLICATIONS

Kieffer, T. et al., Endocrinology, 136(8), 3585–97, Aug. 1995.*

(List continued on next page.)

*Primary Examiner*—Michael Borin
(74) *Attorney, Agent, or Firm*—Mark A. Hofer; Brown, Rudnick Freed & Gesmer (57) ABSTRACT

Novel therapeutic regimens are provided which comprise the administration of therapeutically effective amounts of an inhibitor to dipeptidyl peptidase (DP-IV) or enzymes of similar activity whereby their ability to degrade the incretins, GLP-1 and GIP, is reduced. As a result hyperglycemia, such as that accompanying food intake may be reduced due to improved insulin release. A preferred therapeutic regimen amongst a number of routes of administration and inhibitors that may be used comprises the oral administration of isoleucyl thiazolidine.

9 Claims, 4 Drawing Sheets

OTHER PUBLICATIONS

Mentlein, R. et al. Eur. J. Biochem., 214(3), 829–35, Mar. 1993.*

Deacon C et al. Diabetes, 44 (9) 1126–31, Sep. 1995.*

Hendrick, G.K., Gjinovici, A., Baxter, L.A., Mojsov, S., Wollheim, C.B., Habener, J.F., Weir, G.C.: Glucagon–Like Peptide–I–(7–37) Suppresses Hyperglycemia in Rats. Metabolism 42: 1–6, Jan., 1993.

Deacon, Carolyn F., Johnsen, Andres H., Holst, Jens J.: Degradation of Glucagon–Like Peptide–1 by Human Plasma in Vitro an N–Terminally Truncated Peptide that is a Major Endogenous Metabolite iin Vivo. JCEM 80:952–957, Apr. 25, 1995.

Indications and Citeria for Evaluation for Diabetes Mellitus. ADA Medical Management of Non–Insulin–Dependent (Type II) Diabetes—Third Edition.

Hoffman, Torsten, Reinhold, Dirk, Kahne, Thilo, Faust Jurgen, Neubert, Klaus, Frank Rainer, Ansorge, Siegfried. Inhibition of Dipeptidyle Peptidase IV (DP IV) by anti–DP IV antibodies and non–substrate X–X–Pro– Oligopeptides Ascertained by Capillary Electrophoresis. SSDI 0021–9673(95)00411–4.

Nauck, M.A., Kleine, N., Orskov, C., Holst, J.J., Willms, B., Creutzfeldt, W. Normalization of Fasting Hyperglycaemia by Exogenous Glucagon–Like Peptide 1 (7–36 Amide) in Type 2 (Non–insulin–dependent) Diabetic Patients. Diabetologia 36:741–744, 1993.

Thorens, B. and Waeber, G. Glucagon–Like Peptide–I and the Control of Insulin Secretion in the Normal State and in NIDDM. *Diabetes* 42:1219–1225 (1993).

Orskov, C. et al. Proglucagon Products in Plasma of Non-insulin–dependent Diabetics and Nondiabetic Controls in the Fasting State and after Oral Glucose and Intravenous Arginine. *J. Clin. Invest.* 87:415–423 (1991).

Pauly, R. et al. Improved Glucagon Tolerance in Rats Treated with the Dipeptidyl Peptidase IV (CD26) Inhibitor ILE–Thaxolidide. *Metabolism* 48: 385–389 (1999).

Winslow, R. Novartis Drug Alters Picture for Diabetes. *Wall Street Journal,* Wed. Dec. 27, 2000, p. B2.

Campbell, I.W. New antidiabetc drugs, Sulphonylureas and metformin: efficacy and inadequacy. 3:33–51 (1990).

Mercla Index, 11$^{th}$ Edition, p. 934.

Martindale the Extra, Pharmacopeia, p. 1619.

Chemical Abstracts, vol. 115. No. 15, Oct. 14, 1991 (1991–10–14) Columbus, Ohio, US; abstract No. 149947q, Schoen Ekkehard et al: "Dipeptidyl peptidase IV in the immune system.Effects of specific enzyme inhibitors on activity of dipeptidyl peptidase IV and proliferation of human lymphocytes" Seite 37; XP002114197 Zusammenfassung & Biol. Chem. Hoppe–Seyler, Bd. 372, Nr. 5, 1991, Seiten 305–311.

Chemical Abstracts, vol. 126, No. 2, Jan. 13, 1997 (1997–01–13) Columbus, Ohio, US; abstract No. 16161j, Stoeckel A. et al: "Competitive inhibition of proline specific enzymes by amino acid thioxopyrrolidides and thiazolidides" Seite 241; XP002114198 Zusammenfassung & PEPT: Chem., Struct.Biol., Proc.Am.Pept.Symp., Nr. 14, 1995, Seiten 709–710.

Chemical Abstracts, vol. 118, No. 25, Jun. 21, 1993 (1993–06–21) Columbus, Ohio, US; abstract No. 255342k, Seite 933; XP002114199 Zusammenfassung & JP 04 334357 A (Fujerebio Inc) Nov. 20, 1992 (1992–11–20).

Heihachiro et al: "Synthesis of prolyl endopeptidase inhibitors and evaluation of their structure–activity relationships : in vitro inhibition of prolyl endopeptidase" Chemical and Pharmaceutical Bulletin., Bd. 41, Nr. 9, 1993, Seiten 1583–1588, XP002114196 Pharmaceutical Society of Japan. Tokyo., JP ISSN: 0009–2363 das ganze Dokument.

J. Lin et al.: "Inhibition of depeptidyl peptidase IV by fluoroolefin–containing n–peptidyl–0–hydroxylamine peptidomimetics" Proceedings of the National Academy of Sciences of USA, Bd. 95, Nov. 1998 (1998–11), Seiten 14020–14024, XP002117450 Washington US Seite 14023, rechte Spalte, Absatz 3—Seite 14024, linke Spalte, Absatz 1.

Korom, S., Demeester, I., Stadlbauer, T.H.W., Chandraker, A., Schaub, M, Sayegh, M.H., Belyaev, A., Haemers, A., Scharpe, S., Kupiec–Weglinski, J.W., Inhibition of CD26/dipeptidyl peptidase IV activity in vivo prolongs cardiac allograft survival in rat recipients, Transplantation 63, 1495 (1997).

Tanka, S., Murakmi, T., Horikawa, H., Sugiura, M., Kawashima, K., Sugita, T., Suppression of arthritis by the inhibitors of dipeptidyl peptidase IV. Int. J. Immunopharmacol. 19, 15 (1997).

Mentlein, R., Dahms, P., Grandt, D., Kruger, R., proteolytic processing of neuropeptide Y and peptide YY by dipeptidyl peptidase IV. Regul. Pept. 49, 133 (1993).

Wetzl, W., Wagner, T., Vogel, D., Demuth, H.–U., Balschun, D., Effects of the CLIP fragment ACTH 20–24 on the duration of REM sleep episodes. Neuropeptides, 31, 41 (1997).

Amasheh, S., Wenzel, U., Weber, W.M., Clauss, W., Daniel, H., Electrophysiological analysis of the function of the mammalian renal peptide transporter expressed in *Xenopus laevis* oocytes. J. Physiol. 504, 169–174 (1997).

Wakselman, M., Nguyen, C., Mazaleyrat, J.–P., Callebaut, C., Krust, B., Hovanessian, A.G., Inhibition of HIV–1 infection of CD 26+ but not CD26–cells by a potent cyclopeptidic inhibitor of the DPP IV activity of CD 26. Abstract P 44 of the 24th European Peptide Symposium 1996.

* cited by examiner

Figure 1A:
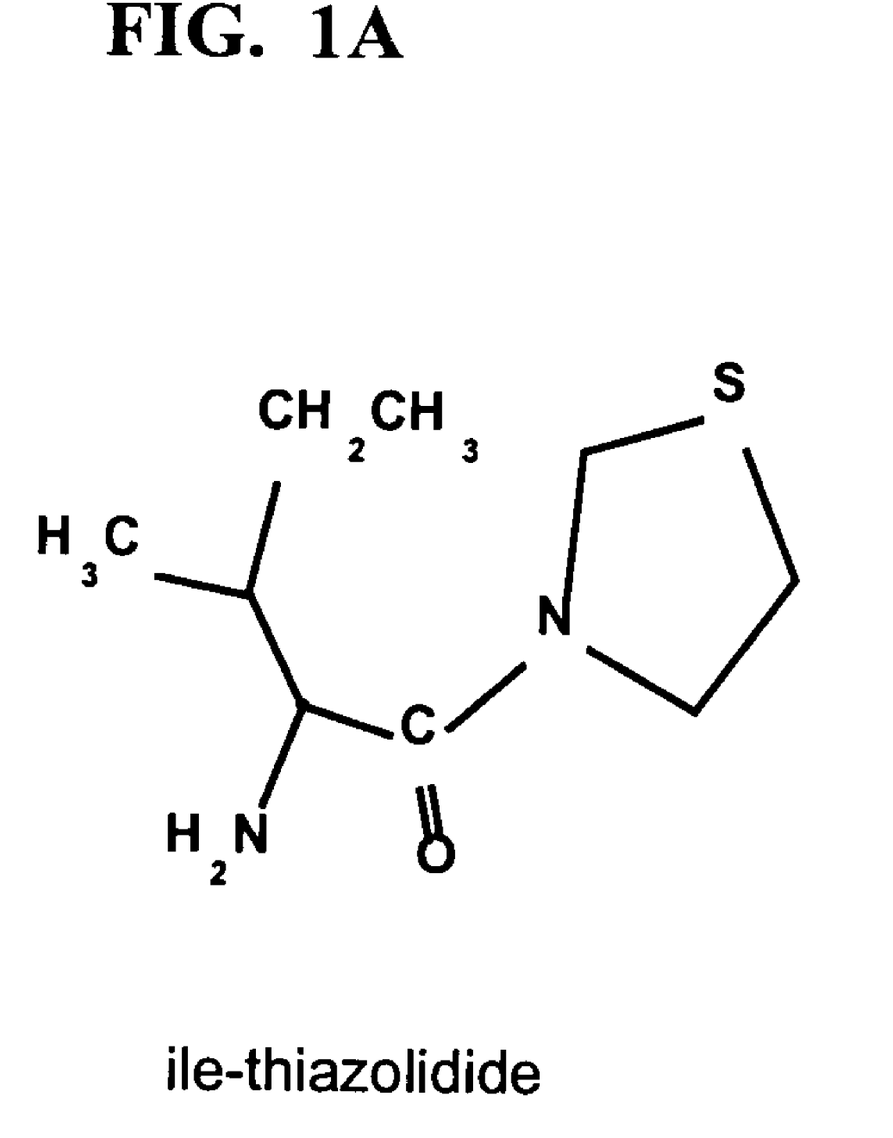

FIG. 1A ile-thiazolidide

USE OF DIPEPTIDYL PEPTIDASE IV EFFECTORS FOR LOWERING THE BLOOD GLUCOSE LEVEL IN MAMMALS

The present invention relates to a novel method for the reduction in the concentration of circulating blood glucose by applying activity lowering effectors (substrates, pseudosubstrates, inhibitors, binding proteins, antibodies and the like) of enzymes with similar or identical activity to the enzymatic activity of the enzyme Dipeptidyl Peptidase IV. Besides proteases involved in non-specific proteolysis, proteases resulting in the specific degradation of proteins are known which are involved in the functional regulation (activation, deactivation or modulation) of endogenous peptides. [KIRSCHKE, H., LANGNER, J., RIEMANN, S., WIEDERANDERS, B., ANSORGE, S. and BOHLEY, P., Lysosomal cysteine proteases. *Excerpta Medica* (Ciba Foundation Symposium 75), 15 (1980); KRÄUSSLICH, H.-G. and WIMMER, E., Viral Proteinases. *Ann. Rev. Biochem.* 57, 701 (1987)].

Such convertases, signal peptidases, or enkephalinases have been discovered in the immune system and as a result of neuropeptide research [GOMEZ, S., GLUSCHANKOF, P., LEPAGE, A., MARRAKCHI, N. and COHEN, P., *Proc. Natl. Acad. Sci. USA* 85, 5468 (1988); ANSORGE, S. and SCHÖN, E., *Histochem.* 82, 41 (1987)].

Since the amino acid proline, which is extraordinarily abundant in numerous peptide hormones, determines certain structural properties of these peptides, proline-specific peptidases have been discussed as having a similar function to the signal peptidases in the regulation of biologically active peptides. [YARON, A., The Role of Proline in the Proteolytic Regulation of Biologically Active Peptides. *Biopolymers* 26, 215 (1987); WALTER, R., SIMMONS, W. H. and YOSHIMOTO, T., Proline Specific Endo- and Exopeptidases. *Mol. Cell Biochem.* 30, 111 (1980); VANHOOF, G. GOOSSENS. F., DE MEESTER, I., HENDRIKS, D. and SCHARPÉ, S., Proline motifs and their biological processing. *FASEB Journal* 9, 736 (1995)]. As a result of its exceptional structure, proline determines in such peptides both their conformation and stability, preventing degradation by non-specific proteases. [KESSLER, H., Conformation and biological activity. *Angew. Chem.* 94, 509 (1982)]. In contrast, enzymes that are capable of highly specific actions on proline-containing sequences (including HIV-protease, cyclophylin, etc) are attractive targets of medicinal chemistry. In particular, the activity of post-proline-cleaving peptidases, such as Prolyl Endopeptidase (PEP) and Dipeptidyl Peptidase IV (DP IV), has been linked to the modulation of the biological activity of natural peptide substrates and their selective cleavage by these enzymes. It has been shown that PEP is involved in memory and learning, and that DP IV participates in signal transduction during the immune response [ISHIURA, S., TSUKAHARA, T. TABIRA, T., SHIMIZU, T., ARAHATA K. and SUGITA, H. *FEBS-Letters* 260, 131 (1990); HEGEN, M., NIEDOBITEK, G., KLEIN, C. E., STEIN, H. and FLEISCHER, B., *J. of Immunology* 144, 2908 (1990)].

In addition to their high proline specificity these enzymes are capable of selectively recognizing and cleaving peptide bonds containing the amino acid alanine in typical substrates. It is at present under discussion as to whether alanine-containing peptides adopt similar conformations to structurally related proline-containing peptides. Recently, such properties have been described by point mutation experiments involving the exchange of proline and alanine in proteins [DODGE, R. W. and SCHERAGA, H. A., Folding and unfolding kinetics of the proline-to-alanine mutants of bovine pancreatic ribonuclease A. *Biochemistry* 35 (5) 1548 (1996)].

DP IV or DP IV-like activity (i.e. the cytosolic DP II possesses almost identical substrate specificity to DP IV) present in the circulation is highly specific in releasing dipeptides from the N-terminal end of biologically active peptides with proline or alanine in the penultimate position of the N-terminal sequence of the peptide substrate. Hence, it has been concluded that this enzyme is involved in the regulation of the activity of polypeptides in vivo [VANHOOF, G., GOOSSENS, F., DE MEESTER, I., HENDRIKS, D. and SCHARPÉ, S., Proline motifs and their biological processing. *FASEB Journal* 9, 736 (1995)].

The glucose-dependent insulinotropic polypeptides: Gastric Inhibitory Polypeptide 1-42 ($GIP_{1-42}$) and Glucagon-Like Peptide Amide-1 7-36 ($GLP-1_{7-36}$), are hormones which potentiate glucose-induced insulin secretion from the pancreas (incretins), and are substrates of DP IV. The enzyme releases the dipeptides tyrosinyl-alanine and histidyl-alanine. respectively from the N-termini of these peptides both in vitro and in vivo. [MENTLEIN, R., GALLWITZ, B., and SCHMIDT, W. E., Dipeptidyl Peptidase IV hydrolyzes gastric inhibitory polypeptide, glucagon-like peptide-1 (7-36) amide, peptide histidine methionine and is responsible for their degradation in human serum. *Eur. J. Biochem.* 214, 829 (1993)].

Reduction in the cleavage of such substrates by DP IV or DP IV-like enzyme activity in vivo can serve to effectively suppress undesirable enzymatic activity under both laboratory conditions and in pathological states in mammals [DEMUTH, H.-U., Recent developments in the irreversible inhibition of serine and cysteine proteases. *J. Enzyme Inhibition* 3, 249–278 (1990); DEMUTH, H.-U. and HEINS. J., On the catalytic Mechanism of Dipeptidyl Peptidase IV. in *Dipeptidyl Peptidase IV* (CD 26) in Metabolism and the Immune Response (B. Fleischer. Ed.) R. G. Landes, Biomedical Publishers, Georgetown, 1–35 (1995)]. For instance, non-insulin dependent Diabetes mellitus is associated with insulin resistance and insulin secretion which is inappropriate for the prevailing glucose concentration, and which may be partially related to protease-mediated abnormalities in the concentration of circulating incretins [BROWN, J. C., DAHL, M., KWAWK, S., MCINTOSH, C. H. S., OTTE, S. C. and PEDERSON, R. A. *Peptides* 2, 241 (1981); SCHMIDT, W. E., SIEGEL, E. G., GALLWITZ, B. KUMMEL, H., EBERT, R. and CREUTZFELDT, W., Characterization of the insulinotropic activity of fragments derived from gastric inhibitory polypeptide. *Diabetologia* 29, 591A (1986); ADELHORST, K., HEDEGAARD, B. B., KNUDSEN, L. B. and KIRK, O., Structure-activity studies of glucagon-like peptide *J. Biol. Chem.* 296, 6275 (1994)].

Insulin-dependent Diabetes mellitus (IDDM) is currently treated through the administration of insulin (isolated from bovine or porcine pancreases or produced as a recombinant molecule) to patients using different forms of administration. Non-insulin-dependent Diabetes mellitus (NIDDM) is treated by diet, administration of sulphonylureas to stimulate insulin secretion or with biguanides to increase glucose uptake. Resistant individuals may need insulin therapy. Traditional, as well as more modem, methods for the treatment of IDDM are characterized by a great deal of effort on behalf of the patient, high costs, and usually a drastic reduction in the quality of living of the patient. Standard therapy (daily i.v. injection of insulin), which has been used since the thirties, is directed at treating the acute symptoms but results, after prolonged application, in vascular disease and nerve damage [LACY, P., Status of Islet Cell Transplantation. *Diabetes Care* 16 (3) 76 (1993)]. More modern methods, such as the installation of subcutaneous depot-implants (insulin release occurring free from proteolytic attack and in small doses, without the need of daily injections) as well as implantation (or transplantation) of intact islet of Langerhans cells are under trial. However, such transplantation is expensive. Additionally, they represent risky surgical intervention and require, in the case of transplantation methods, immunsupression or bypassing the immune response. [LACY, P., Treating Diabetes with Transplanted Cells. *Sci. Americ.* 273 (1) 40–46 (1995)]. Attempts at reducing glucose disposal have not been successful. In the case of NIDDM, many patients treated by stimulating endogenous insulin secretion with sulphonylureas become resistant to these drugs. In addition, increasing glucose disposal with biguanides has met with limited success.

In contrast to the above therapies, the suggested administration of highly effective, low-molecular weight enzyme inhibitors represents a cost-effective alternative. Such inhibitors of various proteolytic enzymes are already in use as anti-hypertensive drugs, immunosuppressive drugs, and antiviral agents. Chemical design of molecules with consideration to their stability, transport and clearance properties may be used to modify their efficacy, and even to adapt the compounds to individual differences between organisms. [SANDLER, M. and SMITH, H. J., eds., *Design of Enzyme Inhibitors as Drugs*. Oxford University Press, Oxford (1989); MUNROE, J. E., SHEPHERD. T. A. JUNGHEIM, L. N., HORNBACK. W. J., HATCH S. D., MUESING, M. A., WISKERCHEN M. A., SU. K. S., CAMPANALE. K. M., BAXTER, A. J., and COLACINO, J. M. Potent, orally bioavailable HIV-1 protease inhibitors containing noncoded D-amino acids. *Bioorg. Medicinal Chem. Letters* 5(23) 2897 (1995)].

The aim of the present invention is a simple and new method to lower the level of blood glucose in which reduction in the activity of the enzyme Dipeptidyl Peptidase (DP IV or CD 26) or of DP IV-like enzyme activity in the blood of mammals induced by effectors of the enzyme will lead to a reduced degradation of the endogenous (or exogenously administrated) insulinotropic peptides Gastric Inhibitory Polypeptide 1-42 ($GIP_{1-42}$) and Glucagon-Like Peptide Amide-1 7-36 ($GLP-1_{7-36}$) (or analogs of these peptides). The decrease in concentration of these peptides or their analogs, normally resulting from degradation by DP IV and DP IV-like enzymes, will thus be reduced or delayed.

The present invention is based on the striking finding that a reduction in the circulating enzymatic activity of Dipeptidyl Peptidase (DP IV or CD 26) or of DP IV-like enzyme activity in the blood of mammals results in an improved glucose tolerance.

We observed that:
1. Reduction of Dipeptidyl Peptidase (DP IV or CD 26) or of DP IV-like enzyme activity leads to a relative increase in the stability of glucose-stimulated endogenously released or exogenously administrated incretins (or their analogs) with the consequence that the administration of effectors of DP IV or of DP IV-like proteins can be used to control the incretin degradation in the circulation.
2. The enhanced biological stability of the incretins (or their analogs) results in a modification of the insulin response.
3. The enhanced stability of the circulating incretins, caused by reduction of Dipeptidyl Peptidase (DP IV or CD 26) or of DP IV-like enzyme, results in subsequent modification of insulin-induced glucose disposal, indicating that glucose tolerance can be improved by applying DP IV-effectors.

Accordingly, the invention concerns the use of effectors of Dipeptidyl Peptidase (DP IV) or of DP IV-like enzyme activity. for lowering of elevated blood glucose levels, such as those found in mammals demonstrating clinically inappropriate basal and post-prandial hyperglycemia. The use according to the invention is more specifically characterized by the administration of effectors of DP IV or of DP IV-analog enzyme activity in the prevention or alleviation of pathological abnormalities of Metabolism of mammals such as glucosuria, hyperlipidaemia, metabolic acidosis and diabetes mellitus. In a further preferred embodiment, the invention concerns a method of lowering elevated blood glucose levels in mammals. Such as those found in a mammal demonstrating clinically inappropriate basal and post-prandial hyperglycemia, comprising administering to a mammal in need of such treatment a therapeutically effective amount of an effector of Dipeptidyl Peptidase (DP IV) or of DP IV-like enzyme activity.

In another preferred embodiment, the invention concerns effectors of Dipeptidyl Peptidase (DP IV) or of DP IV-like enzyme activitv for use in a method of lowering elevated blood glucose Levels in mammals, such as those found in mammals demonstrating clinically inappropriate basal and post-prandial hyperglycemia.

The administered effectors of DP IV and DP IV-like enzymes according to this invention may be employed in pharmaceutical formulations as enzyme inhibitors, substrates, pseudosubstrates. inhibitors of DP IV gene expression, binding proteins or antibodies of the target enzyme proteins or as a combination of such different compounds, which reduce DP IV and DP IV-like protein concentration or enzyme activity in mammals. Effectors according to the invention are, for instance, DP IV-inhibitors such as dipeptide derivatives or dipeptide mimetics as alanyl pyrolidide, isoleucyl thiazolidide as well as the pseudosubstrate N-valyl prolyl, O-benzoyl hydroxylamine. Such compounds are known from the literature [DEMUTH, H.-U., Recent developments in the irreversible inhibition of serine and cysteine proteases. *J. Enzyme Inhibition* 3, 249 (1990)] or may be synthesized according to methods described in the literature.

The method according to the present invention is a new approach to the reduction of elevated circulating glucose concentration in the blood of mammals.

The method is simple, commercially useful and appropriate for use in therapy, especially of human diseases, which are caused by elevated or inappropriate blood glucose levels.

The effectors are administered in the form of pharmaceutical preparations containing the effector in combination with state-of-the-art materials for drug delivery. The effectors are administered either parenterally (i. v. in physiological saline solution) or enterally (oral, formulated with usual carrier materials such as, for example, glucose).

Depending on the endogenous stability and on the bio-availibility of the effectors single or multiple administrations are suitable, to reach the anticipated normalization of the blood glucose concentration. Such dosage range may vary from 1.0 mg to 10.0 mg of effector compound per kilogram, e.g. in the case of the aminoacyl thiazolidides as inhibitors of DP IV.

EXAMPLES

Example 1

Inhibition of the DP IV-catalyzed hydrolysis of the incretins $GIP_{1-42}$ and $GLP-1_{7-36}$ in vivo It is possible to suppress the in vitro hydrolysis of incretins caused by DP IV and DP IV-like enzymatic activity using purified enzyme or pooled human serum (FIG. 1).

Figure 1B:
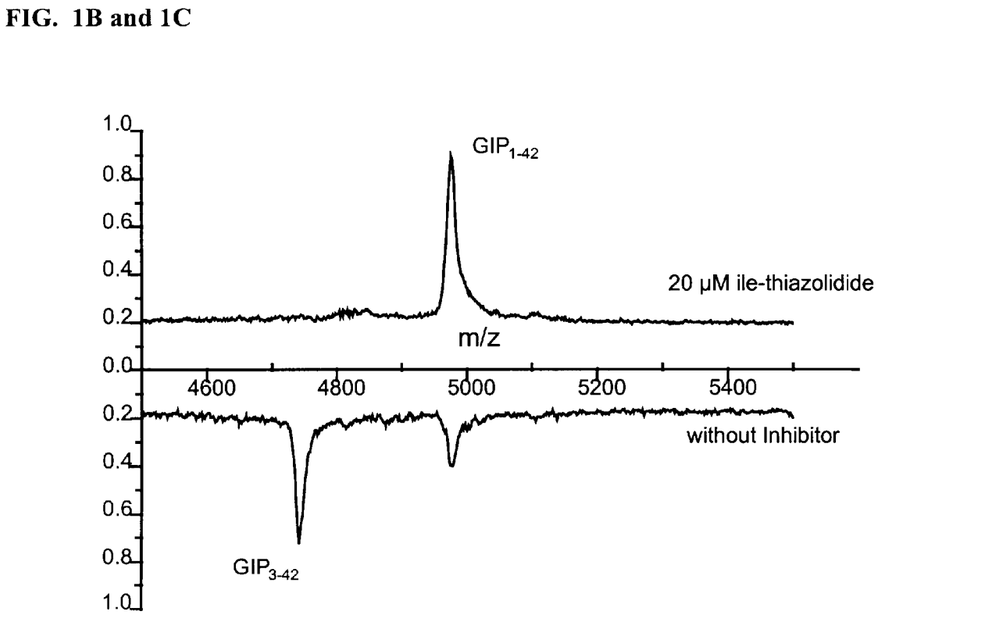
Figure 1C:
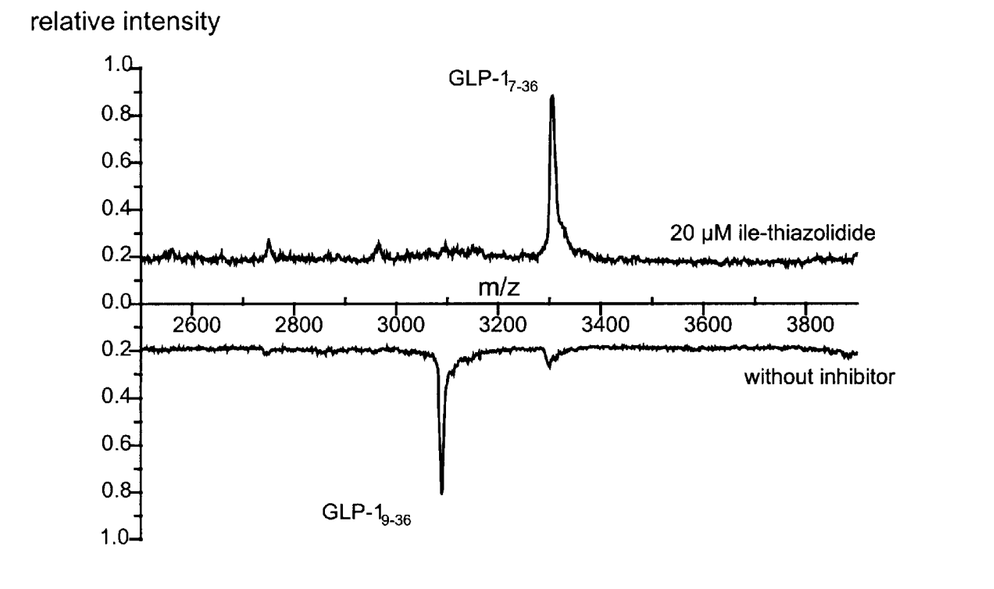

According to the present invention complete suppression of the enzyme-catalyzed hydrolysis of both peptide hormones is achieved in vitro by incubating 30 mM $GIP_{1-42}$ or 30 mM $GLP-1_{7-36}$ and 20 mM isoleucyl thiazolidide (1a), a reversible DP IV-inhibitor in 20% of pooled serum at pH 7.6 and 30° C. over 24 hours (1b and 1c, both upper spectra: Synthetic $GIP_{1-42}$ (5 mM) and synthetic $GLP-1_{7-36}$ (15 μM) were incubated with human serum (20%) in 0.1 mM TRI-CINE Puffer at pH 7.6 and 30° C. for 24 hours. Samples of the incubation assays (in the case of $GIP_{1-42}$ 2.5 pmol and in the case of $GLP-1_{7-36}$ 7.5 pmol) have been withdrawn after different time intervals. Samples were cocrystallized using 2',6'-dihydroxyacetophenon as matrix and analyzed by MALDI-TOF-mass spectrometry. Spectra (FIG. 1) display accumulations of 250 single laser shots per sample.

(1b) The signal of m/z 4980.1±5.3 corresponds to the DP IV-substrate $GIP_{1-42}$, (M 4975.6) and the signal of the mass m/z 4745.2±5.5 corresponds to the DP IV-released product $GIP_{3-42}$ (M 4740.4).

(1c) The signal of m/z 3325.0±1.2 corresponds to the DP IV-substrate $GLP-1_{7-36}$ (M 3297.7) and the signal of mass m/z 3116.7±1.3 to the DP IV-released product $GLP-1_{9-36}$ (M 3089.6).

In the control assays containing no inhibitor the incretins were almost completely degraded (FIG. 1b and 1c, both bottom spectra).

Example 2

Inhibition of the degradation of $GLP1_{7-36}$ by the DP IV-inhibitor isoleucyl thiazolidide in vivo.

Figure 2:
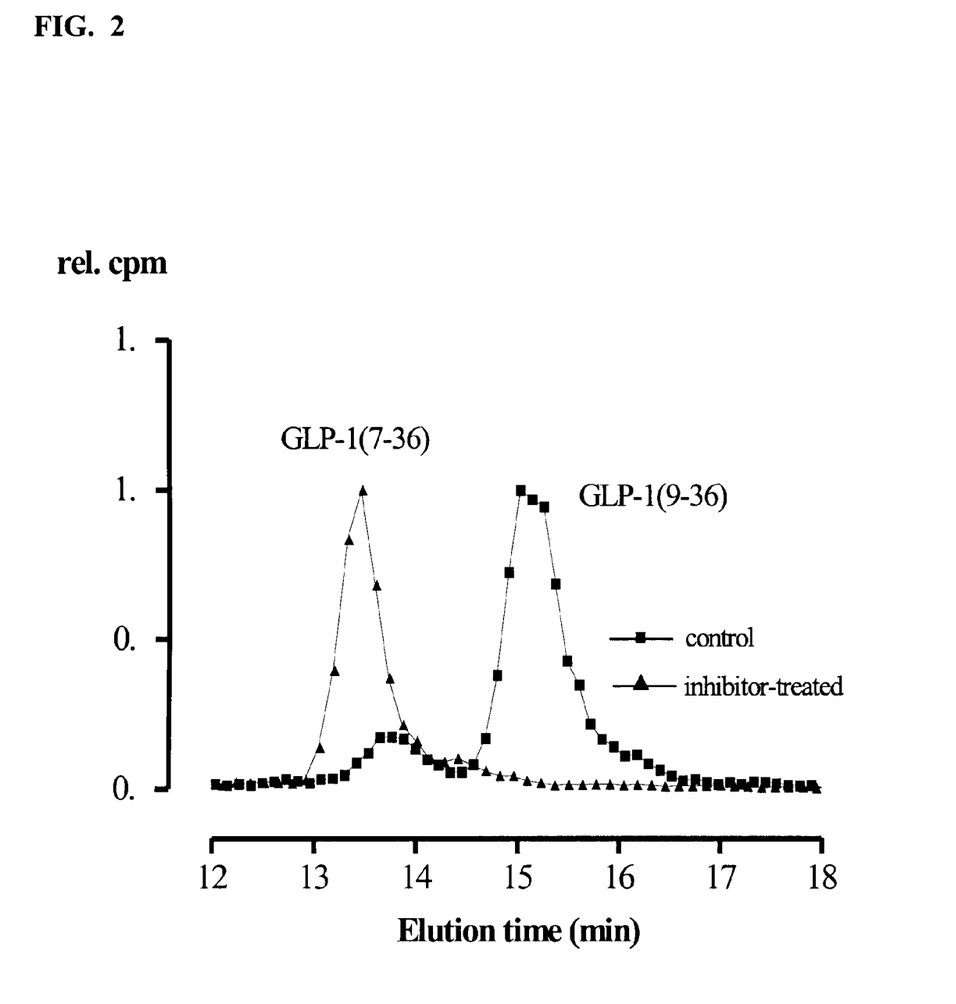

Analysis of the metabolism of native incretins (in this case $GLP-1_{7-36}$) in the circulation of the rat in the presence or absence of the DP IV-inhibitor isoleucyl thiazolidide (i.v. injection of 1.5 M inhibitor in 0.9% saline solution) and of a control. No degradation of the insulinotropic peptide hormone $GLP-1_{7-36}$ occurs at a concentration of 0.1 mg/kg of the inhibitor isoleucyl thiazolidide in treated animals (n=5) during the time course of the experiment (FIG. 2).

To analyze the metabolites of the incretins in the presence and absence of the DP IV-inhibitor, test and control animals received a further i.v. injection of 50–100 pM $^{125}$I- $GLP-1_{7-36}$ (specific activity about 1 μCi/pM) 20 min after an initial i.v. -inhibitor and/or saline administration. Blood samples were collected after 2–5 min incubation time and the plasma was extracted using 20% acetonitrile. Subsequently, the peptide extract was separated on RP-HPLC. Multiple fractions of eluent were collected between 12–18 min and counted on a γ-counter. Data are expressed as counts per minute (cpm) relative to the maximum.

Example 3

Modulation of insulin responses and reduction of the blood glucose level after i.v. administration of the DP IV-inhibitor isoleucyl thiazolidide in vivo.

Figure 3A:
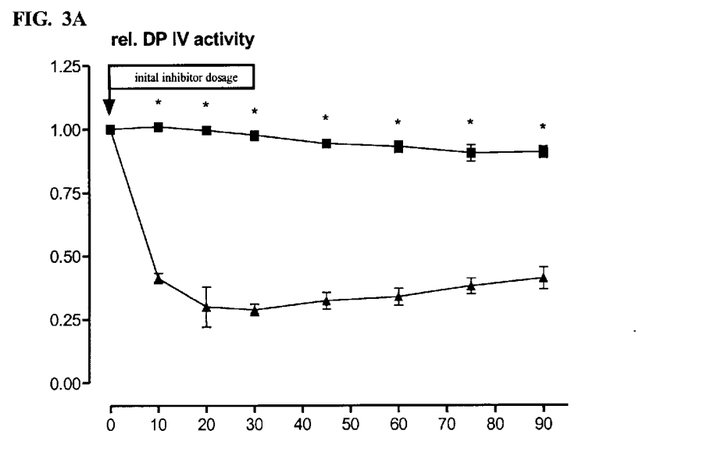
Figure 3B:
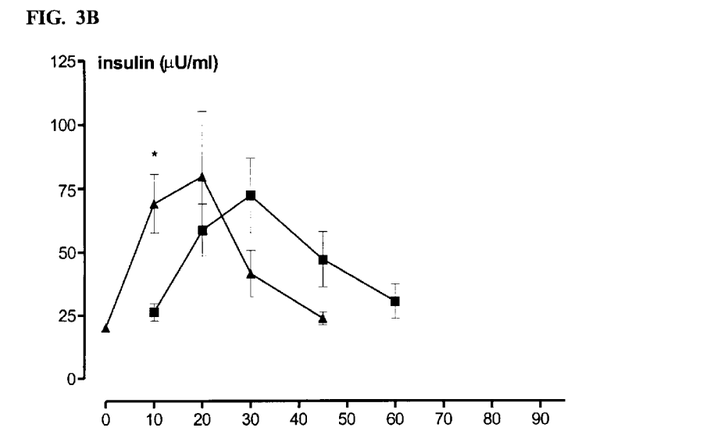
Figure 3C:
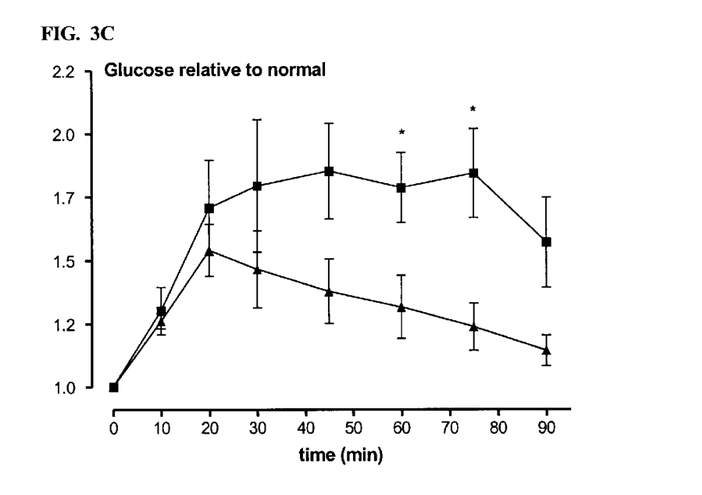

The figure shows circulating glucose and insulin responses to intraduodenal (i.d.) administration of glucose to rats in the presence or absence of isoleucyl thiazolidide (0.1 mg per kg). There is a more rapid reduction in the circulating glucose concentration in animals, which received DP IV-effectors when compared to untreated controls. The observed effect is dose dependent and reversible after termination of an infusion of 0.05 mg/min of the DP IVinhibitor isoleucyl thiazolidide per kg rat. In contrast to the i.d. glucose-stimulated animals, there was no comparable effect observable after the i.v. administration of the same amount of glucose in inhibitor-treated control animals. In FIG. 3 these relationships are demonstrated displaying the inhibitor-dependent changes of selected plasma parameter: A-DP IV-activity. B-plasma-insulin level C-blood glucose level.

The test animals (n=5, male Wistar-rats, 200–225 g) initially received 1.5 M IsoleucylThiazolidide in 0.9% saline solution (♦) or the same volume of plain 0.9% saline solution (■) (control group n=5). The test group additionally obtained an infusion of the inhibitor of 0.75 M/min over 30 min experimental time (★). The control group received during the same time interval an infusion of inhibitor-free 0.9% saline solution. At starting time t=0 all animals were administered an i.d. glucose dose of 1 g/kg 40% dextrose solution (w/v). Blood samples were collected of all test animals in 10 min time intervals. Glucose was analyzed using whole blood (Lifescan One Touch II analyzer) while DP IV-activity and insulin concentration were analyzed in plasma. The insulin radioimmunoassay was sensitive over that range 10 and 160 mU/ml [PEDERSON, R. A., BUCHAN, A. M. J., ZAHEDI-ASH, S., CHEN, C. B. & BROWN, J. C. *Reg. Peptides*. 3, 53–63 (1982)]. DP IV-activity was estimated spectrophotometrically [DEMUTH, H.-U. and HEINS. J., On the catalytic Mechanism of Dipeptidyl Peptidase IV. in *Dipeptidyl Peptidase IV* (CD 26) *in Metabolism and the Immune Response* (B. Fleischer, Ed.) R. G. Landes, Biomedical Publishers, Georgetown, 1–35 (1995)]. All data are presented as mean +/- s.e.m.

SUMMARY OF THE INVENTION

The present invention relates to a novel method in which reduction of the activity of the enzyme Dipeptidyl Peptidase (DP IV or CD 26), or of DP IV-like enzyme activity, in the blood of mammals by specific enzvme effectors will result in a reduced degradation of the endogenous, or exogenously administrated, insulinotropic peptides (incretins), Gastric Inhibitory Polypeptide/Glucose-dependent Insulinotropic Polypeptide 1-42 ($GIP_{1-42}$) and Glucagon-like Peptide-1 7-36 amide ($GLP-1_{7-36}$) (or analogs of these peptides). The decrease in concentration of these peptides or their analogs, resulting from degradation by DP IV and DP IV-like enzymes, will be thus be reduced or delayed.

As a consequence of the enhanced stability of the endogenous, or exogenously administrated, incretins or their analogs, caused by a reduction in DP IV-activity, their insulinotropic effects are enhanced, resulting in a potentate stimulation of insulin secretion from the pancreatic islets of Langerhans, and more rapid removal of glucose from the blood. As a result, glucose tolerance is improved.

As a consequence, metabolic abnormalities associated with Diabetes mellitus, including abnormalities of carbohydrate and lipid metabolism, glucosuria and severe metabolic acidosis, and chronic alterations such as microvascular and macrovascular disease and polyneuropathy, which are the consequence of prolonged, elevated circulating glucose concentrations, are prevented or alleviated.

The present invention is a new approach to lowering elevated concentrations of blood glucose. It is simple, commercially useful, and is suitable to be used in the therapy, especially of human diseases, which are caused by elevated or extraordinary blood glucose levels.

We claim:

1. A method for lowering elevated blood glucose levels in mammals resulting from food intake comprising administering at least one oral administration of a therapeutically effective amount of at least one inhibitor of Dipeptidyl Peptidase (DP IV) or of DP IV-like enzyme activity.

2. The method according to claim 1, wherein said at least one inhibitor is selected from the group consisting of alanyl pyrrolidine, isoleucyl thiazolidine, and N-valyl prolyl, O-benzoyl hydroxylamine.

3. The method according to claim 1, wherein said at least one inhibitor is administered in combination with at least one carrier substance.

4. The method according to claim 1, wherein said at least one inhibitor is administered in multiple administrations.

5. The method according to claim 1, wherein said amount is between 1.0 mg to 10.0 mg per kilogram of the inhibitor compound.

6. The method according to claim 1, wherein the mammals demonstrate clinically inappropriate basal and postprandial hyperglycemia.

7. The method according to claim 1, wherein the administration is for the prevention or alleviation of pathological abnormalities of metabolism of mammals such as glucosuria, hyperlipidaemia, metabolic acidosis and Diabetes mellitus.

8. A method for lowering elevated blood glucose levels in mammals resulting from food intake comprising the administration of a therapeutically effective amount of an inhibitor of DP-IV enzyme activity comprising isoleucyl thiazolidine.

9. A method for lowering elevated blood glucose levels in mammals resulting from food intake comprising the oral administration of a therapeutically effective amount of an inhibitor of DP-IV enzyme activity selected from the group consisting of alanyl pyrrolidine and isoleucyl thiazolidine.

* * * * *

UNITED STATES PATENT AND TRADEMARK OFFICE
CERTIFICATE OF CORRECTION

PATENT NO.   : 6,303,661 B1                                          Page 1 of 1
DATED        : October 16, 2001
INVENTOR(S)  : Demuth et al.

It is certified that error appears in the above-identified patent and that said Letters Patent is hereby corrected as shown below:

Column 6,
Lines 63-67, Claim 1 should read as follows:
1. A method for lowering elevated post-prandial blood glucose levels in mammals comprising administering at least one oral administration of a therapeutically effective amount of at least one inhibitor of Dipeptidyl Peptidase (DP IV) or DP IV-like enzyme activity.

Column 8,
Lines 6-9, Claim 8 should read as follows:
8. A method for lowering elevated post-prandial blood glucose levels in mammals comprising the administration of a therapeutically effective amount of an inhibitor of DP-IV enzyme activity comprising isoleucyl thiazolidine.

Lines 10-14, Claim 9 should read as follows:
9. A method for lowering elevated post-prandial blood glucose levels in mammals comprising the oral administration of a therapeutically effective amount of an inhibitor of DP-IV enzyme activity selected from the group consisting of alanyl pyrrolidine and isoleucyl thiazolidine.

Signed and Sealed this

Twenty-third Day of December, 2003

JAMES E. ROGAN
*Director of the United States Patent and Trademark Office*